United States Patent [19]

Ondeyka et al.

[11] Patent Number: 5,091,389
[45] Date of Patent: Feb. 25, 1992

[54] LIPOPHILIC MACROLIDE USEFUL AS AN IMMUNOSUPPRESSANT

[75] Inventors: John Ondeyka, Fanwood; Otto Hensens, Red Bank; Jerrold Liesch, Princeton Junction, all of N.J.

[73] Assignee: Merck & Co., Inc., Rahway, N.J.

[21] Appl. No.: 690,407

[22] Filed: Apr. 23, 1991

[51] Int. Cl.⁵ .................. A61K 31/395; C07D 491/16
[52] U.S. Cl. .................. 514/291; 540/456; 540/452
[58] Field of Search ............. 540/546, 542; 514/291, 514/63

[56]            References Cited
         U.S. PATENT DOCUMENTS

| | | | |
|---|---|---|---|
| 3,929,992 | 12/1975 | Sehgal et al. | 424/124 |
| 4,316,885 | 2/1982 | Rakhit | 546/90 |
| 4,401,653 | 8/1983 | Eng | 424/114 |
| 4,650,803 | 3/1987 | Stella et al. | 514/491 |

OTHER PUBLICATIONS

H. Baker et al., J. Antibiotics, vol. 31 (6) pp. 539–545.
J. P. Devlin and K. D. Hargrave, Tetrahedron, vol. 45 (14), pp. 4327–4369 (1989).
C. P. Eng et al., J. Antibiotics, vol. 37 (10) pp. 1231–1237 (1984).
J. A. Findlay and L. Radics, Can. J. Chem., vol. 58, pp. 579–590 (1980).
J. A. Findlay et al., Can. J. Chem., vol. 60, pp. 2046 (1982).
M. W. Harding et al., Nature, vol. 341, pp. 758–760 (1989).
S. N. Sehgal et al., J. Antibiotics, vol. 28 (10), pp. 727–732 (1975).
S. N. Sehgal et al., J. Antibiotics, vol. 36 (4), pp. 351–354 (1983).
K. Singh et al., J. Antibiotics, vol. 32 (6), pp. 630–645 (1979).
S. M. Stepkowski et al., Transplantation Proc., vol. 23 (1), pp. 507–508 (1991).
M. J. Tocci, J. Immunology, vol. 143 (2), pp. 718–726 (1989).
C. Vezina, J. Antibiotics, vol. 28 (10), pp. 721–726 (1975).

Primary Examiner—Robert T. Bond
Attorney, Agent, or Firm—Curtis C. Panzer; Hesna J. Pfeiffer

[57]           ABSTRACT

Disclosed is a novel lipophilic macrolide of assigned Formula I:

The compound of assigned Formula I is an analog of rapamycin which has activity as an antifungal agent and as an immunosuppressant.

3 Claims, 1 Drawing Sheet

LIPOPHILIC MACROLIDE USEFUL AS AN IMMUNOSUPPRESSANT

BACKGROUND OF THE INVENTION

This invention relates to macrolides having activity as an antifungal agent and as an immunosuppressant.

In particular, this invention relates to analogs of the compound rapamycin, which is a compound of the following formula:

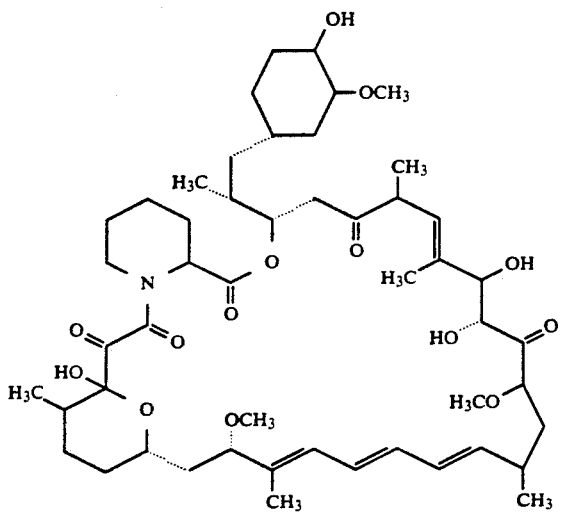

which is useful as an antifungal agent and is useful in the suppression of the immune response.

As early as 1975, rapamycin was identified as an antifungal antibiotic harvested from a Streptomyces hygroscopicus culture, which culture was isolated from an Easter Island soil sample. See Vezina et al., J. Antibiot. 28, 721-726 (1975); and U.S. Pat. No. 3,929,992, which issued to Sehgal, et. al. Dec. 30, 1975. The ability of this compound to inhibit the immune response was first described by Martel, R. et al., Can. J. Physiol. Pharmacol., 55, 48-51 (1977). In this work, the authors show the utility of this compound in inhibiting the response to allergic encephalomyelitis, adjuvant-induced arthritis and antibody production in rats. More recently, Calne, R. Y. et al., has shown rapamycin to be immunosuppressive in rats given heterotopic heart allografts. Calne, R. Y. et al., Lancet vol. 2, p. 227 (1989). Equally important, less toxicity was said to be experienced than would be anticipated with FK-506 (U.S. Pat. No. 4,894,366, assigned to Fujisawa, which issued on Jan. 16, 1990), with which rapamycin shares some structural features.

More recently, rapamycin has been shown to be useful in combination therapy with Cyclosporin A. This combination has the advantage of reducing the amount of Cyclosporin A required to produce its immunosupressive effect, such as in heart, kidney, bowel, pancreas or other transplantation, and thereby effectively reducing the nephrotoxicity inherent in treatment with Cyclosporin A. See Stepkowski, S. M. et al., Transplantation Proceedings, vol. 23, pp 507-508 (1991).

As appreciated by those of skill in the art, and as exemplified by Harding, M. W. et al., Nature, vol. 341, p. 758-760 (1989) and Devlin, J. P. and Hargrave, K. D. Tetrahedron, vol. 45, p. 4327-4369 (1989), Cyclosporin A, FK-506, rapamycin, and analogs thereof, can be expected to share a broad range of utilities as immunosuppressive agents. Cyclosporin A, FK-506, rapamycin and analogs thereof find utility in the prevention of rejection or organ and bone marrow transplants; and in the treatment of psoriasis, and a number of autoimmune disorders such as type 1 diabetes mellitus, multiple sclerosis, autoimmune uveitis, and rheumatoid arthritis. Additional indications are discussed infra.

SUMMARY OF THE INVENTION

This invention relates to a compound of assigned Formula I:

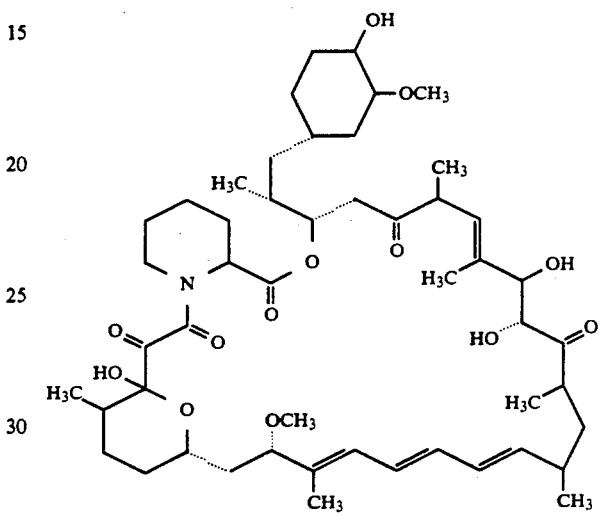

which compound is a useful antifungal agent and immunosuppressive agent.

DETAILED DESCRIPTION OF THE INVENTION

Figure 1:
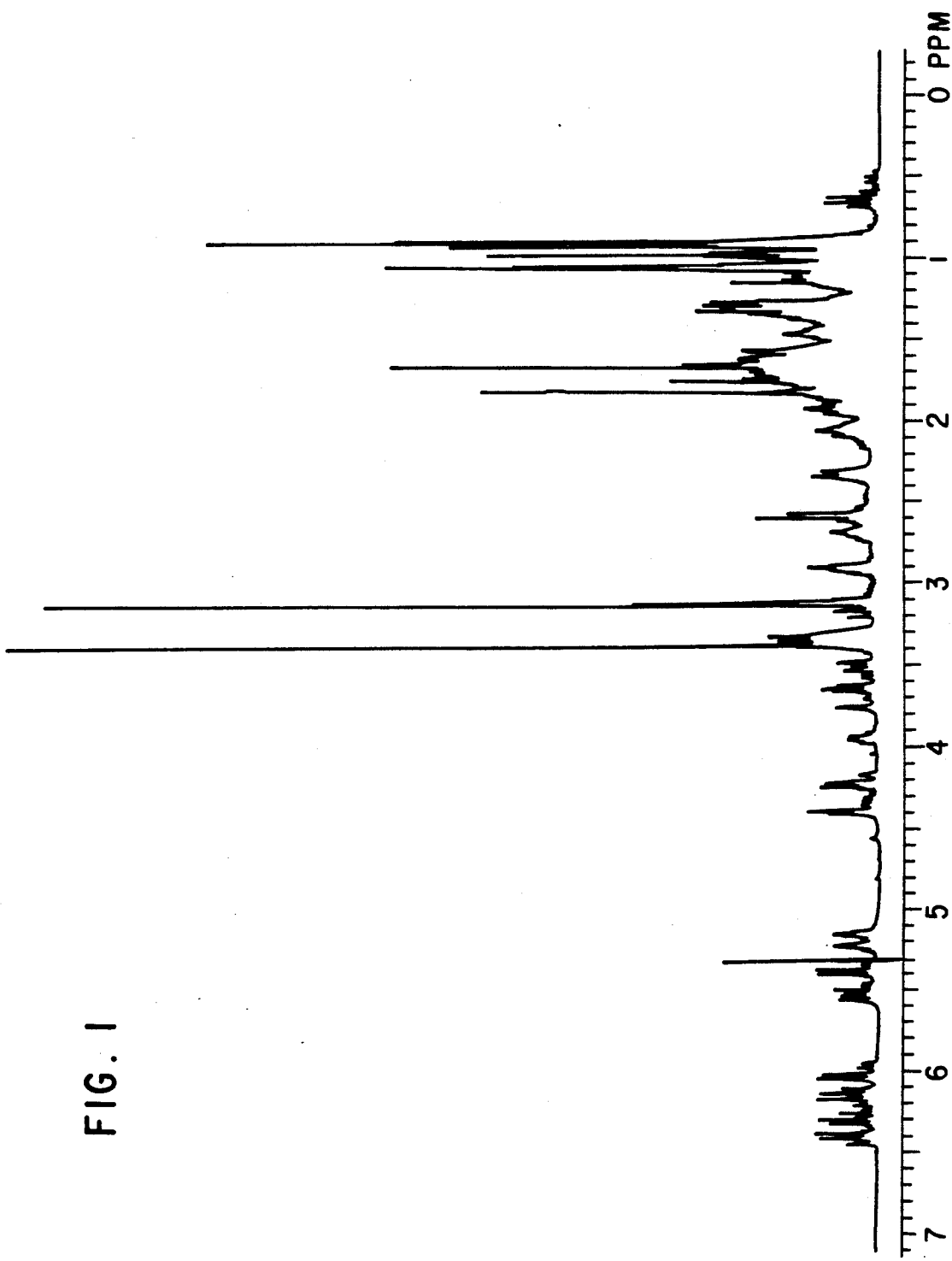
FIG. 1 is the 400 MHz $^1$H-NMR spectrum of the compound of assigned Formula I recorded in $CD_2Cl_2$.

This invention relates to a compound of Formula I,

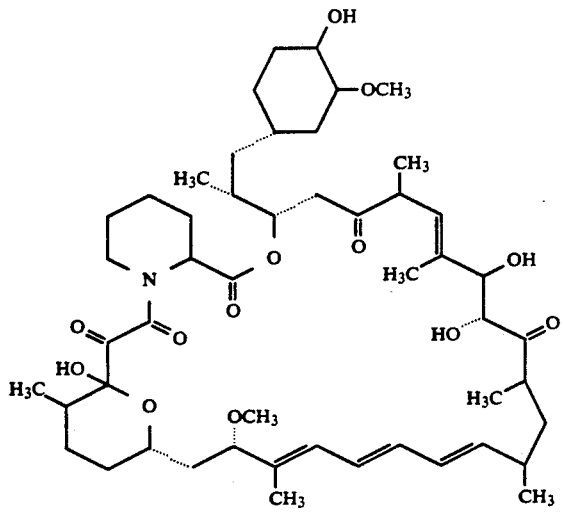

The compound of Formula I may also be described as 29-desmethyl rapamycin. The invention also relates to substantially pure compound of assigned Formula I. For purposes of this specification substantially pure shall designate a purity in excess of 98% and free of rapamycin.

This invention also relates to pharmaceutical compositions for inducing immunosuppression in a subject in need of such treatment, comprising: administration of a therapeutically effective amount of 29-desmethyl rapamycin.

In view of its immunosuppressive activity, 29-desmethyl rapamycin is useful for the prophylaxis and treatment of diseases and conditions requiring a reduction of the immune response. Thus it may be used to suppress the proliferation of lymphocytes and immunocytes, e.g. in treatment of autoimmune diseases or in preventing the rejection of transplants e.g. skin, lung, heart, heart-lung, bone-marrow, kidney, spleen and corneal transplants.

Specific auto-immune diseases for which the compound of formula I is useful includes all of those for which treatment with cyclosporin A and/or FK-506 has been proposed or used, for example, aplastic anaemia, pure red cell anaemia, isopathic thrombocytopaenia, systemic lupus erythematosus, polychondritis, scleroderma, Wegener granulomatosis, chronic active hepatitis, myasthenia gravis, psoriasis, Steven-Johnston syndrome, idiopathic sprue, Crohn's disease, Graves opthalmopathy, sarcoidosis, multiple sclerosis, primary biliary cirrhosis, primary juvenile diabetes, uveitis posterior, interstitial lung fibrosis and psoriatic arthritis as well as insulin-dependent diabetes mellitus, nephrotic syndrome and AIDS.

This invention also relates to a pharmaceutical compositions for inducing immunosuppresion in a subject in need of such treatment, comprising a therapeutically effective amount of Cyclosporin A and 29-desmethyl rapamycin.

This invention also relates to a method of inducing immunosuppression in a subject in need of such treatment, comprising administration of a therapeutically effective amount of 29-desmethyl rapamycin.

The compound of assigned Formula I can be conveniently prepared by fermentation of a culture of Streptomyces hygroscopicus such as NRRL 5491, which strain can be obtained from the culture collection at the National Center for Agricultural Utilization Research, USDA, ARS, Peoria, Ill. NRRL 5491 is also available from the American Type Culture Collection, Rockville, Md. as as ATCC 29253. This organism, and procedures for its cultivation are described in Vezina et al., J. Antibiot. 28, 721-726 (1975); Sehgal et al J. Antibiot. 28, 727-732, and U.S. Pat. No. 3,929,992; said references being hereby incorporated by reference.

As appreciated by those of skill in the art, microorganisms for production of 29-desmethyl rapamycin may include other natural or artificial mutants or variants derived from the described culture. The artificial production of mutant strains may be achieved by physical or chemical mutagens, for example, ultraviolet irradiation or N-nitrosoguanidine treatment and the like. Recombinant DNA techniques such as protoplast fusion, plasmid incorporation, gene transfer and the like are also envisioned.

In general cultivation of NRRL 5491 can be carried out by conventional aerobic fermentation of suitable nutrient media which contain sources of assimilable carbon, nitrogen and inorganic salts.

In general, many carbohydrates such as glucose, maltose, mannose, sucrose, starch, glycerin, millet jelly, molasses, soy bean and the like can be used as sources of assimilable carbon. Sources of assimilable nitrogen includes such materials as yeast and casein hydrolysates, primary yeast, yeast extracts, cottonseed flour, soybean solids, wheat germ, meat extracts, peptone, corn steep liquor, and ammonium salts. The inorganic salt nutrients which can be incorporated in the culture medium are the customary salts yielding sodium, iron, magnesium, potassium, cobalt, phosphate and the like. In general, of course, the techniques employed will be chosen having regard to industrial efficiency. The nutrient media described herein are merely illustrative of the wide variety of media that may be employed and are not intended to be limiting.

The fermentation has been carried out at temperatures ranging from about 22° C. to 32° C.; however, for optimum results it is preferable to conduct the fermentation at about 28° C. The pH of the medium is controlled at about pH 6-7 by the use of suitable organic or inorganic buffers incorporated into the fermentation medium or by periodic addition of a base. Good yields of 29-desmethyl rapamycin can be achieved within 48 to 72 hours. Variation of the medium or the microorganism will alter the yield of the compound of 29-desmethyl rapamycin and/or its rate of production. The preferred media compositions are set forth in the examples.

Specific examples of fermentation isolation and recovery conditions we have found to be advantageous are provided in the Examples Section below.

As stated above, in view of its immunosuppressive activity, 29-desmethyl rapamycin is useful for the prophylaxis and treatment of diseases and conditions requiring a reduction of the immune response. Thus they may be used to suppress the proliferation of lymphocytes and immunocytes, e.g. in treatment of autoimmune diseases or in preventing the rejection of transplants e.g. skin, lung, heart, heart-lung, bone-marrow, kidney, spleen and corneal transplants.

Specific auto-immune diseases for which the 29-desmethyl rapamycin are useful include all of those for which treatment with cyclosporin and FK-506 have been proposed or used, for example, aplastic anaemia, pure red cell anaemia, isopathic thrombocytopaenia, systemic lupus erythematosus, polychondritis, scleroderma, Wegener granulomatosis, chronic active hepatitis, myasthenia gravis, psoriasis, Steven-Johnston syndrome, idiopathic sprue, Crohn's diseases, Graves opthalmopathy, sarcoidosis, multiple sclerosis, primary biliary cirrhosis, primary juvenile diabetes, uveitis posterior, interstitial lung fibrosis and psoriatic arthritis as well as insulin-dependent diabetes mellitus, nephrotic syndrome and AIDS.

Moreover, the compound of assigned Formula I can be used in combination therapy with Cyclosporin A as discussed in Stepkowski, S. M. et al., Transplantation Proceedings, vol. 23, pp 507-508 (1991), which is hereby incorporated by reference.

In addition the compound of assigned Formula I can be used as an antifungal agent.

For all these uses the dosage will, of course, vary depending on the compound employed, mode of administration and treatment desired. However, in general, satisfactory results are obtained when administered at a daily dosage of from about 1 mg to about 200 mg per kg animal body weight, conveniently given in divided doses 2 to 4 times a day or in sustained release form. For the larger mammals, the total daily dosage is in the range from about 50 to about 5000 mg, and dosage forms suitable for oral mg (e.g. 25-300 mg) of the compounds admixed with a solid or liquid pharmaceutical carrier or diluent.

The present invention also provides a pharmaceutical composition comprising a compound of formula I such as in association with a pharmaceutical carrier or diluent.

Such compositions may be in the form of, for example, a solution, a tablet or a capsule and in ointments especially for the treatment of psoriasis.

29-desmethyl rapamycin may be administered by any conventional route, in particular in accordance with means currently practiced in relation to administration of cyclosporin, in particular via intravenous infusion, e.g. in the case of organ transplant, pre- and immediately post-transplant, as well as during episodes of gastrointestinal disturbance which might otherwise impair absorption, or orally, e.g. in the form of an oral solution.

Biological activity as a immunosupressant can be measured in terms of inhibition of T-cell proliferation.

T-cell proliferation was measured in mouse T-cell cultures stimulated with ionomycin plus phorbol myristate acetate (PMA). Spleen cell suspensions from C57B1/6 mice were prepared and separated on nylon wool columns. The recovered T-cells were suspended at $10^6$ cells/ml in complete culture medium with addition of ionomycin (250 ng/ml) and PMA (10 ng/ml). The cell suspension was immediately distributed in 96 well-flat bottom microculture plates at 200 μl/well. Control medium or various concentrations of test compound were added in triplicate wells at 20 μl/well. Parallel cultures were set up with exogenous IL-2 (50 units/ml). The plates were incubated as 37° C. in a humidified atmosphere of 5% $CO_2$-95% air for 44 hours. The cultures were then pulsed with tritiated-thymidine (2 uCi/well) for an additional 4 hour period and cells were collected on fiber glass filters using a multisample harvester. Incorporated radioactivity was measured in a BETAPLATE COUNTER (PHARMACIA/LKB, Piscataway, N.J.) and the mean count per minute (cpm) values of triplicate samples calculated. The percent inhibition of proliferation was calculated according to the formula:

$$\% \text{ Inhib.} = 100 - \frac{\text{mean cpm experimental}}{\text{mean cpm control medium}} \times 100$$

This assay is described in detail in Dumont, F. J. et al, J. Immunol. (1990) 144:251

| INHIBITION OF T CELL PROLIFERATION STIMULATED WITH IONOMYCIN + PMA BY 29-DESMETHYL RAPAMYCIN | |
|---|---|
| 29-desmethyl-rapamycin Concentration (μM) | Percent Inhibition of Proliferation |
| 11.2 | 88 |
| 1.2 | 59 |
| 0.12 | 49 |
| 0.01 | 32 |
| 0.001 | 7 |

29-desmethyl-rapamycin was found to inhibit the proliferation of mouse T cells stimulated with ionomycin+PMA. Under the same conditions, 1.1 μM rapamycin inhibited the proliferation by 65%. As for rapamycin, the inhibitory activity of 29-desmethyl-rapamycin was not reversed by exogenous IL-2 (50 units/ml).

EXAMPLE 1

PRODUCTION OF 29-DESMETHYL RAPAMYCIN 29-desmethyl rapamycin is produced from fermentation of Streptomyces Hydroscopicus NRRL 5491. The seed train was developed through four stages as following:

a) first stage is B flask (250 ml unbaffled Erlenmeyer flask) with 40 ml of seed medium as: yeast extract FIDCO 20 g/1, HY-CASE SF 20 g/1, cerelose 20 g/1, potassium nitrate 2 g/1, POLYGLYCOL (as antifoam) 0.3 ml/1 and trace elements mix as: $FeSO_4$ $6H_2O$ 0.025 g/1, NaCl 0.5 g/1, $MgSO_4$ $7H_2O$ 0.5 g/1, $MnSO_4$ $H_2O$ 0.005 g/1, $ZnSO_4$ $7H_2O$ 0.01 g/1, $CaCl_2$ $2H_2O$ 0.02 g/1, sterilized as 121° C. for 25 min. is inoculated with 0.3 ml of suspended in sterile water spore inoculum, and incubated at 28° C. for 72 hours on the 220 rpm shaker.

b) second stage of seed in C flask (2000 ml unbaffled Erlenmeyer flask) with 500 ml seed medium is inoculated with 7.5 ml of first stage and incubated at 28° C. for 48 hours on 220 rpm shaker.

c) third stage of seed is cultivated in 300 liters (75 gallons) stainless steel agitated fermenter with temperature, pH and DO control. Fermenter with 180 liters of seed medium previously sterilized at 121° C. for 20 min. is inoculated with three C flasks of second stage seed (0.8% inoculum) and grow at 27° C. for 68 hours.

Production stage is run in 800 liters (200 gallons) stainless steel agitated fermenter equipped with automatic temperature, air flow, back pressure, pH and dissolved oxygen controllers. All fermenters are charged with 500 liters of an aqueous production medium consisting of the following ingredients: cerelose 20 g/1, NUTRISOY 30 g/1, glycerol 20 g/1, L-lysine 4 g/1, ammonium sulfate 5 g/1 potassium phosphate monobasic 2.5 g/1, potassium phosphate dibasic 2.5 g/1, and POLYGLYCOL P-2000 (as antifoam agent) 2 ml/1. The media are sterilized at 121° C. for 25 min., cooled to 27° C. and the pH is adjusted with sodium hydroxide to 6.5 before the seed introduction to production medium. All batches are inoculated with 25 liters (5% inoculum) of third stage seed and 88 hours of fermentation cycle is controlled at temperature 27° C., pH 6-7 and 50% of oxygen saturation.

EXAMPLE 2

Isolation of 29-Desmethyl Rapamycin from Fermentation Broth 330 gallons of fermentation broth was dewatered via a WESTFALIA decanter. The product was extracted into approximately 250 gallons of methanol from the cell cream to yield approximately 253 gallons of methanol extract. The cell cream was again extracted into about 75 gallons of methanol to yield about 78 gallons of extract. The methanol extracts were combined and concentrated partially in a vacuum evaporator to 85 gallons. The extract was then washed twice with hexane (80 gallons each wash) and further concentrated to 25 gallons. The product in the concentrated methanol solution was extracted into ethyl acetate via two extractions. The ethyl acetate extracts (approximately 16 gallons each) were combined and concentrated to 5 gallons. Precipitates of impurities that formed during concentration were filtered off. Filtrate was loaded onto a 20-gallon silica gel column, which had been equilibrated with 30/70% acetone/hexane solution. The column was then eluted with 10 bed volumes of 30/70% acetone/hexane solution, and fractions of 5 gallons in size were collected. The cut richest in rapamcyn like compound (e.g. cuts 12 to 18) were then concentrated further.

The combined rich cuts containing about 12 G of rapamycin in 3 liters of ethyl acetate was charged to a 30 gallon silica gel column (GRACE silica) and eluted with 3:1, hexane:acetone. 36 5-gallon cuts were taken and rapamycin found in cuts 11-19. Cuts were analyzed by silica TLC and HPLC. WHATMAN silica gel 60 TLC plates were used with a 95:5, methylene chloride:methanol solvent system and visulization was by UV or iodine staining. WHATMAN ODS-3 analytical column was used with a SPECTRA PHYSICS 8700 pumping system at 40 C using methanol:water (8-2) at a flow rate of 1.5 min/ml monitoured at 277 nM. The retention time was 8.5 min. Four related minor components were detected in cuts 9-10 and 16-20 based on uv ratio by HPLC. Cuts 16-20 were dissolved in etoac/hex/ace and charged to a 2 liter silica gel column in 3;1 hexane:acetone. Cuts 36-46 contained rapamycin while cuts 47-50 contained some minor components as well as cuts 51-52. Cuts 51-52 (0.5 g) was dissolved in 3 ml methanol and 1 ml charged to a 25 cc×22 mm DS-3 column and eluted with methanol:water (8-2) at 7 ml/min and 7 ml cuts collected. This was repeated twice. Cuts 23-25, from all 3 chromatographies, contained compound 1 (25 mg). This material was subjected to NMR and MS studies as well as biological assay.

FAB-MS

Cuts 23-25 was found to have a molecular weight of 899 as determined by FAB-MS (observed (M+Na) at m/z 922, and in the lithium spiked spectrum (M+Li) at m/z 906. In contrast to rapamycin, the m/z 541 ion is absent in the EI spectrum; but a new ion is observed at m/z 527.

$^1$H NMR

The 1H NMR spectrum of cuts 23-25 in $CD_2Cl_2$ is shown in FIG. 1. The spectrum was recorded at 400 MHz on a VARIAN XL400 NMR spectrometer at 21° C. Chemical shifts are shown in ppm relative to TMS at zero ppm using the solvent peak at 5.32 ppm as the internal standard.

What is claimed is:

1. A compound of Formula I,

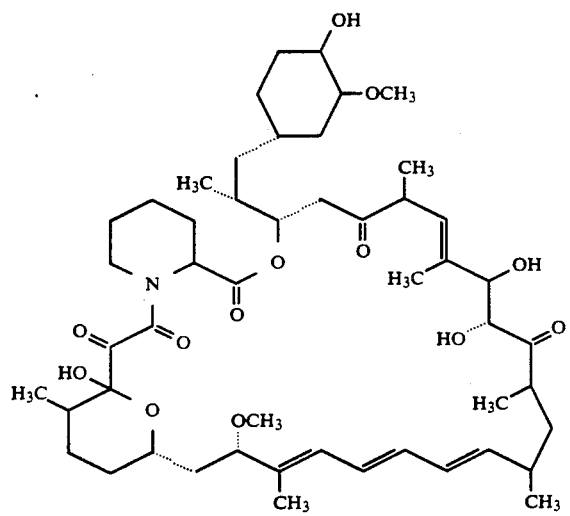

or a pharmaceutically acceptable salt thereof.

2. A pharmaceutical compositions for inducing immunosuppression in a subject in need of such treatment, comprising:
a pharmaceutical carrier and a therapeutically effective amount of compound according to claim 1.

3. A method of inducing immunosuppression in a subject in need of such treatment, comprising administration to said subject a non toxic therapeutically effective amount of compound according to claim 1.

* * * * *